United States Patent [19]

Isaacs et al.

[11] Patent Number: 4,881,545
[45] Date of Patent: Nov. 21, 1989

[54] SURGICAL FASTENER CARTRIDGE WITH IMPROVED BODY TISSUE CUTTING KNIFE ASSEMBLY

[75] Inventors: Jack L. Isaacs, Trumbull, Conn.; Boris Zvenyatsky, Bronx, N.Y.

[73] Assignee: United States Surgical Corporation, Norwalk, Conn.

[21] Appl. No.: 281,552

[22] Filed: Dec. 8, 1988

[51] Int. Cl.⁴ .............................................. A61B 17/04
[52] U.S. Cl. ................................... 227/178; 128/305; 227/19; 227/901
[58] Field of Search ............. 128/334 R, 305; 227/19, 227/DIG. 1

[56] References Cited

U.S. PATENT DOCUMENTS 4,617,928 10/1986 Alfranca ............................... 128/305
4,665,916 5/1987 Green ............................... 128/334 R
4,676,245 6/1987 Fukuda ............................ 128/334 C
4,788,978 12/1988 Strekopytov et al. .......... 128/334 R

FOREIGN PATENT DOCUMENTS 1069794 1/1984 U.S.S.R. .......................... 128/334 R

Primary Examiner—Edward M. Coven
Assistant Examiner—Gary Jackson
Attorney, Agent, or Firm—Dilworth & Barrese

[57] ABSTRACT

A surgical fastener cartridge possesses an improved body tissue cutting knife assembly. The knife element of the assembly is held in permanent and irreversible locking engagement with a knife holder which is advantageously formed from a single piece of thermoplastic resin possessing two opposed sides joined through at least one flexible hinge element.

10 Claims, 5 Drawing Sheets

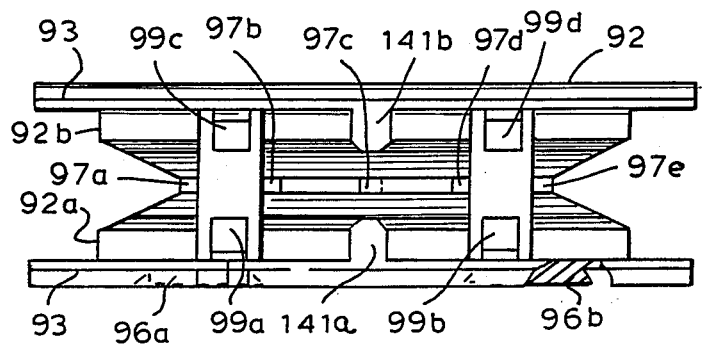
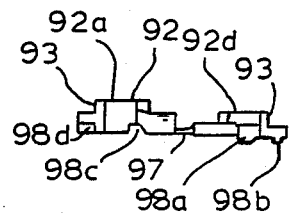
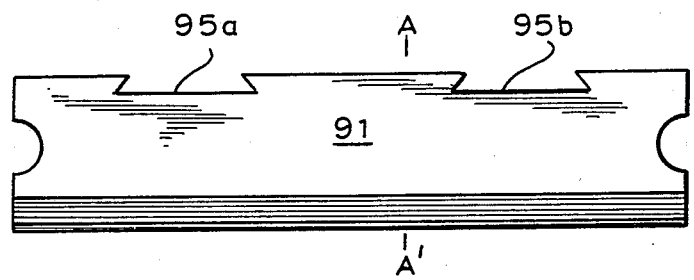
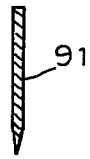
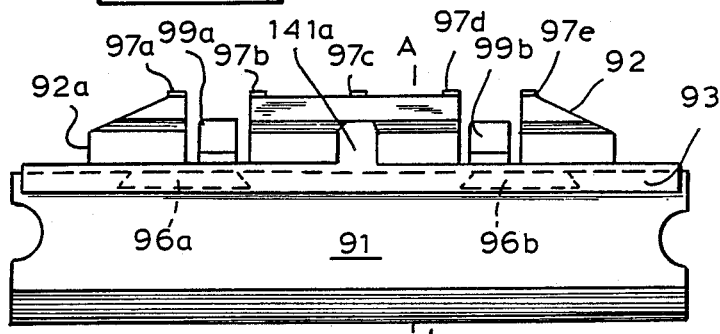
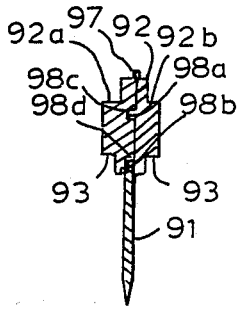
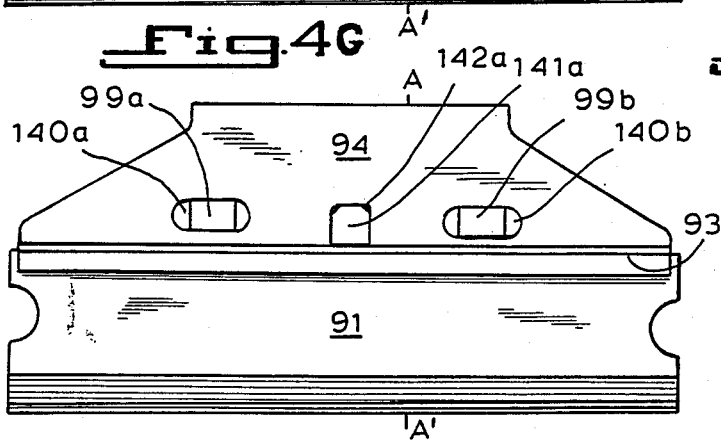
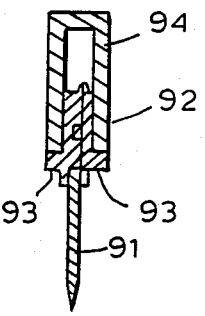

SURGICAL FASTENER CARTRIDGE WITH IMPROVED BODY TISSUE CUTTING KNIFE ASSEMBLY

BACKGROUND OF THE INVENTION

This invention relates to a surgical fastener cartridge possessing an improved body tissue cutting knife assembly. The cartridge is adapted for use with a known type of surgical cartridge actuator apparatus, actuation of which causes rows of fasteners to be applied to body tissue and an incision to be formed between the rows, the fasteners providing effective hemostasis for the incision.

Surgical fastener applicator apparatus in which surgical fasteners are simultaneously applied to body tissue are known. Typically, these devices include a fastener holder positioned on one side of the tissue to be fastened, an anvil parallel to the fastener holder positioned on the other side of the tissue, means for linearly translating the fastener holder and the anvil toward one another so that the tissue is clamped between them, and means for driving the fasteners from the fastener holder so that the ends of the fasteners pass through the tissue and form finished fasteners as they make contact with the anvil assembly, thereby producing an array of finished fasteners in the tissue.

In common use are apparatus in which the fastener holder and anvil are removably mounted in or on an actuator for supporting and actuating the cartridge. The cartridge can be disposed of after a single use or it can be reused for another surgical fastening procedure after cleaning, sterilizing and reloading with a fresh cartridge. Also in use are fully disposable surgical instruments in which the cartridge and actuator are preassembled ready for use and disposed of after only a single use.

Although instruments of the type described above are available for performing several different types of surgical fastening procedures, an illustrative type of instrument is the so-called thoracic-abdominal surgical fastener which is typically used for applying rows of fasteners laterally through hollow body organs such as the thorax, trachea, stomach, uterus or intestines.

U.S. Pat. No. 4,665,916, the contents of which are incorporated by reference herein, describes a surgical fastener apparatus of the foregoing type. The cartridge includes an alignment pin which achieves and maintains proper relative positioning of the fastener holder and anvil components thereof. When the fully assembled instrument is about to be actuated, it is positioned in such a way that the body tissue to be fastened is clamped in place between the staple-ejecting surface of the fastener holder and the clamping pressure exerted against both sides of the tissue is sufficient to provide effective hemostasis along two linear sites which, upon actuation, or "firing", of the instrument, receive substantially parallel rows of fasteners on either side of an incision formed by a tissue cutting knife, also incorporated in the holder, the deployment of which is mechanically synchronized to immediately follow the insertion of the fasteners.

SUMMARY OF THE INVENTION

In a surgical fastener cartridge which is adapted for use with an actuator apparatus having a rigid frame and a generally U-shaped portion for receiving the fastener cartridge, the actuator apparatus actuating the fastener cartridge to apply substantially parallel rows of fasteners to the tissue on both sides of a line of incision formed by a body tissue cutting knife assembly included within the fastener cartridge, said fastener cartridge possessing:

(a) a fastener holder containing a quantity of fasteners, the fasteners being driven, upon actuation of the fastener cartridge, through substantially parallel rows of apertures defined upon a fastener ejecting surface of the fastener holder;

(b) an anvil having a surface opposed to the fastener ejecting surface of the fastener holder and, upon actuation of the fastener cartridge, cooperating therewith to apply substantially parallel rows of fasteners to body tissue positioned between the fastener holder and anvil;

(c) means for driving the fasteners through the apertures upon actuation of the fastener cartridge;

(d) a tissue cutting knife assembly including (i) a knife element having an upper non-cutting edge and a lower cutting edge, (ii) a knife holder engaging the upper edge of the knife element and (iii) a knife pusher enclosing the knife holder, the cutting edge of the knife element being recessed within the fastener holder in the non-actuated condition of the fastener cartridge and, upon actuation of the fastener cartridge, extending beyond a slot formed between the rows of apertures; and, (e) means for driving the cutting edge of the knife assembly through the slot upon actuation of the fastener cartridge, an improvement is provided which comprises a knife holder having two opposed sides defining at their lower sections a groove therebetween, the knife element being received into, and held in permanent and irreversible locking engagement with, the groove.

The term "fasteners" is used herein as a generic term for metal surgical staples, the staple-shaped portion of two-part resinous surgical fasteners, and their equivalents. Similarily, the term "anvil" is used herein as a generic term to include an anvil which is used to clinch metal surgical staples, a holder for the retainer member of a two-part resinous surgical fastener, and the equivalent of these elements. The term "permanent and irreversible locking engagement" describes a mechanical arrangement in which the knife holder cannot be separated from the knife element without causing permanent damage to either or both of these elements, an arrangement which contrasts with the potentially reversible engagement of knife holder and knife element characteristic of prior art knife assemblies, e.g., that described in U.S. Pat. No. 4,665,916, referred to supra, wherein the knife element is adhesively bonded to the knife holder within a groove formed in the latter.

DETAILED DESCRIPTION OF THE DRAWINGS

Figures 1A, 1B:
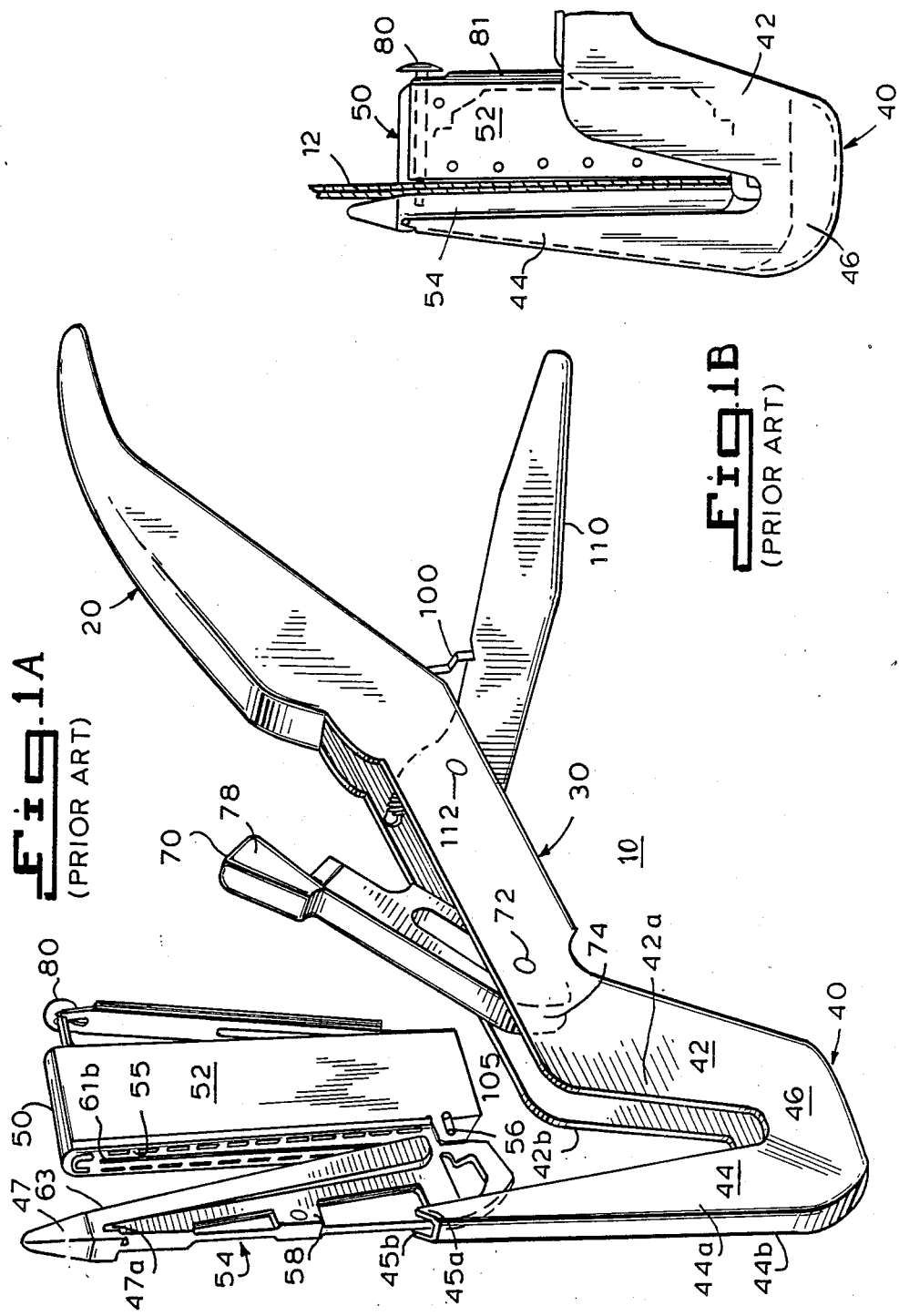
Figure 2:
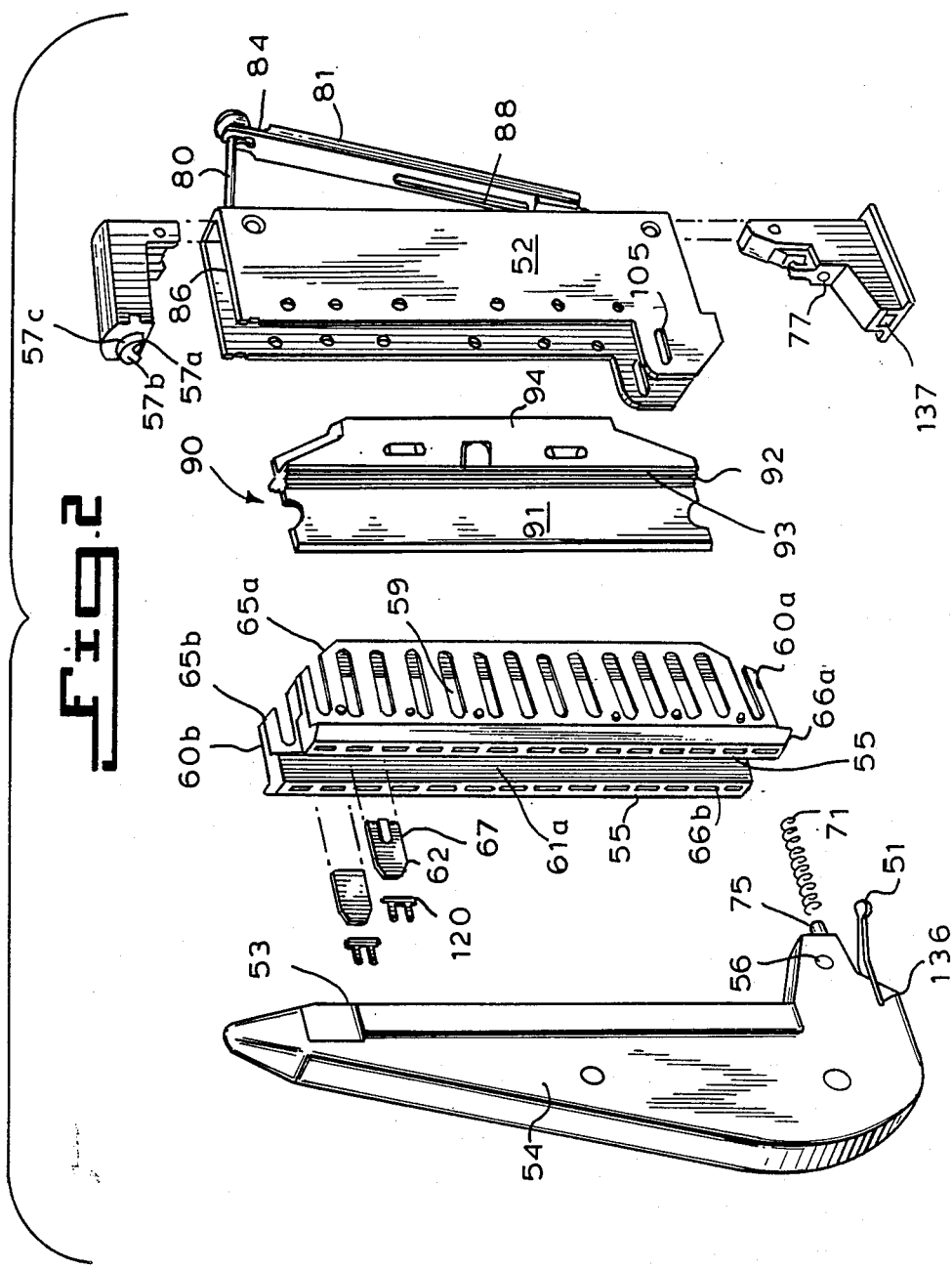
Figure 3A:
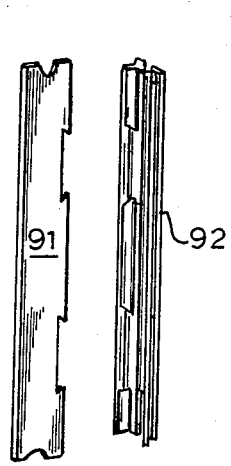
Figure 3B:
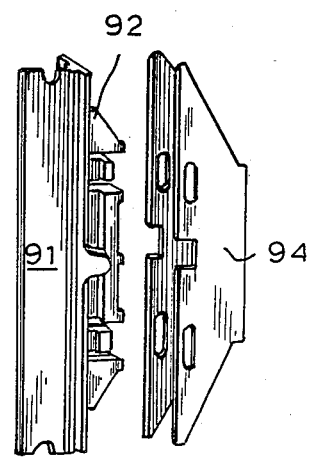
Figure 3C:
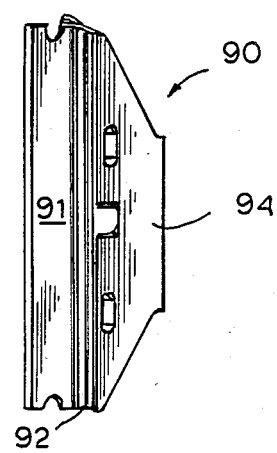
Figure 5:
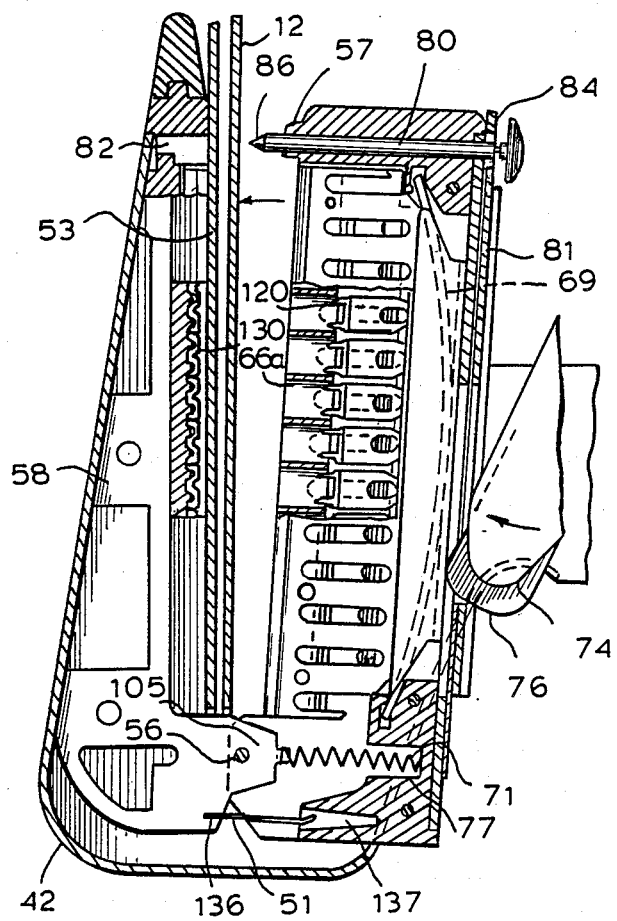

FIGS. 1A and 1B illustrate, respectively, a perspective view of the surgical fastener applicator device of U.S. Pat. No. 4,665,916 showing the fastener cartridge about to be inserted in the actuator frame and an enlarged elevational view of a part of the fully assembled applicator device showing body tissue clamped in place and ready to be fastened and cut;

FIG. 2 is an exploded perspective view of a fastener cartridge similar to that shown in FIGS. 1A and B but possessing an improved body tissue cutting knife assembly in accordance with the present invention;

FIGS. 3A–C are perspective views of subassemblies (FIGS. 3A and B) and the fully assembled (FIG. 3C) improved body tissue cutting knife assembly of FIG. 2;

FIGS. 4A–H are enlarged views of the individual elements comprising the improved tissue cutting knife assembly of FIGS. 3A–C with FIGS. 4A and 4B illustrating, respectively, plan and cross-sectional views of the knife holder prior to being formed about the knife element, the latter being shown in side elevational and cross-sectional views, respectively, in FIGS. 4C and 4D, and with FIGS. 4E and 4F illustrating, respectively, side elevational and cross-sectional views of the knife holder and knife element sub-assembly, the full knife assembly being shown in side elevational and cross-sectional views, respectively, in FIGS. 4G and 4H; and, FIG. 5 is an enlarged sectional view of a part of the fastener cartridge of FIG. 2 showing the operation of the device to cut and fasten body tissue.

DESCRIPTION OF THE PREFERRED EMBODIMENTS

FIGS. 1A and 1B are presented by way of illustrating a known type of fastener cartridge actuator apparatus, i.e., that described in U.S. Pat. No. 4,665,916, which can be used in conjunction with the fastener cartridge of this invention featuring an improved surgical knife assembly. As shown in FIGS. 1A and 1B, the known type of actuator device includes a handle 20 adjacent the proximal end of the instrument, a longitudinal connecting structure 30 and an approximately U-shaped or V-shaped support structure 40 at the distal end of connecting structure 30. Support structure 40 comprises a proximal leg 42, a distal leg 44, and a base 46 joining one end of each of legs 42 and 44. Support structure 40 lies in a plane substantially parallel to the longitudinal axis of connecting structure 30. In use, the instrument is positioned relative to tissue 12 to be fastened so that the tissue is generally between legs 42 and 44 and transverse to the plane of support structure 40.

Disposable fastener cartridge 50, shown in FIG. 1A about to be inserted within leg 44 of support structure 40 and in FIG. 1B, fully seated within said structure, includes fastener holder 52 and anvil support 54. Anvil support 54 is mounted into distal leg 44 and fastener holder 52 is mounted into proximal leg 42. The end of cartridge 50 at which pivotal axis 56 is located is inserted into base 46. Pivotal axis 56 allows pivotal motion of fastener holder 52 and anvil 54 relative to each other and, together with slots 105, also allows a limited amount of motion of the fastener holder perpendicular to anvil surface 53.

Anvil support 54 is designed to slide longitudinally into and out of leg 44 of support structure 40. The distal side of anvil support 54 features a retaining structure 58 which fits between plates 44a and 44b of distal leg 44. Cartridge 50 is releasably retained within leg 44 by a friction fit between retaining structure 58 and plates 44a and 44b, and is positioned accurately in the longitudinal direction of leg 44 by the fit between projections 45a and 45b and cutouts (not shown) at the corresponding ends of anvil support 54. When cartridge 50 is positioned in support structure 40 and projections 45a and 45b are located against the cutouts, anvil support 54 will be located between plates 42a and 42b of proximal leg 42.

Disposable cartridge 50 of FIGS. 1A and 1B, incorporating the improved body tissue cutting knife assembly of this invention, is shown in detail in the exploded perspective view of FIG. 2 and in the sectional view of FIG. 5. As shown in these drawings, fastener holder 52 accommodates a pair of pusher holders 60a and 60b, each possessing a row of fastener-containing apertures, 66a and 66b, respectively, with each aperture containing a fastener 120. Surface 53 of anvil support 54 directly opposite that of the fastener ejecting surfaces of fastener storage elements 65a and 65b possesses two rows of fastener retainer-containing apertures (not shown) in opposed alignment with fastener-containing apertures 66a and 66b with each of said retainer-containing apertures containing an individual fastener retainer element 130 which is capable of locking with the prongs of an individual fastener 120 upon actuation of the device. Behind each fastener 120 is a fastener pusher 62 slidably mounted in pusher holders 60a and 60b. During the fastener ejection sequence, tissue cutting knife assembly 90 is driven in the distal direction along a passageway 61a located between pusher holders 60a and 60b and terminating in a slot 61b (shown in FIG. 1A). As the knife assembly moves, shoulder 93 of knife holder 92 contacts the proximal ends of fastener pushers 62 thus causing pushers 62 to be moved in the distal direction along guide slots 59 into which projections 67 of the pushers extend. Access to knife assembly 90 is through an elongated slot in the proximal side of fastener holder 52 and elongated slot 88 in spring 81, to be discussed in more detail below. Fastener holder 52 normally is biased away from anvil support 54 by leaf spring 51 and coil spring 71. One end of leaf spring 51 is retained within slot 136 of anvil support 54. The other end of leaf spring 51 bears against surface 137 inside fastener holder 52. Spring 71 biases pivotal axis 56 to the distal end of slots 105 and is kept in place by projection 75 and cylindrical space 77.

Fastener holder 52 also carries alignment pin 80. In order to prevent the end of alignment pin 80 from partly obstructing the open end of cartridge 50 when the cartridge is open (which could present a possible hazard to the tissue being placed in, or removed from, the instrument), the pin is reciprocally mounted in fastener holder 52 and provided with means for its automatic extension during the fastening operation and its automatic retraction when cartridge 50 is opened. The proximal end of pin 80 is engaged by the slotted end 84 of leaf spring 81 which extends along the proximal side of fastener holder 52 and is anchored at the bottom of fastener holder 52. Leaf spring 81 possesses an elongated slot 88 which is generally co-extensive with a slot formed in fastener holder 52. Leaf spring 81 is so arranged that it will normally be inclined away from the proximal side of fastener holder 52 in the direction toward pin 80. In this condition, spring 81 holds pin 80 in the retracted position so that distal end 86 of pin 80 does not project from fastener holder 52. As shown in FIG. 5, distal end 86 of alignment pin 80 is advantageously provided with a point in order to enable the pin to easily pierce tissue 12 as the pin is extended beyond fastener ejecting surface 55 during the fastening operation.

As shown in FIGS. 1A and 5, when tissue 12 is placed between fastener holder 52 and anvil support 54, pivoting clamp actuator 70 is pivoted clockwise about its pivotal axis 72 causing camming surface 74 on the distal end of actuator 70 to pivot fastener holder 52 counterclockwise about its pivotal axis 56 thereby gradually clamping tissue 12 between fastener holder 52 and opposing anvil surface 53. When actuator 70 has been fully pivoted clockwise so that it is substantially parallel to the longitudinal axis of connecting structure 30 as shown in FIG. 1B, tissue 12 is then firmly clamped between anvil support surface 53 and opposing fastener ejecting surface 55. As fastener holder 52 closes on tissue 12, alignment pin 80 pierces the tissue and spacer member 57 displaces the tissue surrounding pin 80 and contacts anvil surface 53. Elongated apertures 105 allow pivotal axis 56 to translate linearly in the proximal direction through a relatively short distance thereby resulting in fastener ejecting surface 55 and opposed anvil surface 53 being parallel to each other and ready for the firing of fasteners 120 into the tissue clamped therebetween.

As fastener holder 52 is pivoted counterclockwise by actuator 70, the tissue which would otherwise prevent spacer member 57 from contacting anvil surface 53 is displaced by sloping surfaces 57a and 57b of spacer member 57 (FIG. 1A). These surfaces slope towards each other to form a knife-like edge which displaces the tissue and permits the furthest-most projection, i.e., surface 57c of spacer member 57, to abut against anvil surface 53. Proper alignment of fastener holder 52 and anvil support is aided by alignment pin 80 which extends through the side of fastener holder 52 opposite pivotal axis 56 and into alignment pin aperture 82 (FIG. 5) in anvil support 54 as fastener holder surface 55 is pivoted parallel to anvil surface 53. As fastener holder 52 is pivoted counterclockwise, alignment pin 80 extends past spacer member 57 and makes contact with, and pushes through, the tissue located in front of alignment pin aperture 82. As fastener holder 52 continues to pivot counterclockwise, spacer member 57 reaches the tissue and begins to displace the tissue which is now surrounding alignment pin 80. When fastener holder 52 is fully pivoted, spacer member 57 has displaced the tissue so as to abut against anvil surface 53 and ensure parallel alignment betwenn fastener holder surface 55 and anvil surface 53.

As shown in FIGS. 2, 3A-C and 4A-H, tissue cutting knife assembly 90 is fabricated from a knife element 91 surmounted by knife holder 92 which in turn is enclosed by knife pusher 94. The knife holder is advantageously provided as a single piece of molded thermoplastic, e.g., a polycarbonate such as Makrolon (Bayer) or Lexan (General Electric), and possesses hinge elements 97a-e which are capable of at least one full flexure. Knife holder 92 is oriented with respect to knife element 91 in such a manner that upon folding of the knife holder about hinge elements 97a-e during the knife assembly manufacturing procedure, upwardly projecting locking members 96a (shown by the dotted line in FIG. 3A) and 96b (shown in the partial cutaway view in FIG. 3A) engage key elements 95a and 95b formed along the upper non-cutting edge of knife element 91. Permanent joining of opposed faces 92a and 92b of knife holder 92 can be achieved in any convenient manner, e.g., employing a suitable adhesive, and as shown, is preferably accomplished by the known technique of ultrasonic welding, optionally supplemented by adhesive bonding. Joining of faces 92a and 92b results in mating engagement of ultrasonic welding bumps 98a and 98b defined on the interior wall of side 92b of the knife holder with corresponding ultrasonic welding pockets 98c and 98d, respectively, defined on the interior wall of side 92a of the knife holder and locking engagement of locking elements 96a and 96b defined upon the lower edge of the interior wall of side 92a of the knife holder with corresponding key elements 95a and 95b formed upon the upper edge of knife element 91. Up-raised locking elements 99a-d provide sliding irreversible locking engagement with corresponding cut-outs 140a-d (cut-outs 100c and 100d are not shown) formed in knife pusher 94 and guide elements 141a and 141b lock with cut-outs 142a and 142b (cut-out 142b is not shown) so as to facilitate accurate positioning of knife pusher 94 on knife holder 92 during assembly of these components. The space between the two opposed sides of the knife holder in effect constitutes a locking groove within which knife 91 is permanently and irreversibly locked, a particularly advantageous construction since it eliminates any possibility that the knife element will accidentally disengage from the knife holder during actuation of the fastener cartridge cycle. In contrast to the highly secure locking groove feature of the improved knife holder herein, the known type of knife holder, e.g., that described in U.S. Pat. No. 4,665,916, referred to supra, possesses a smooth continuous slot lacking lock-and-key or other functionally equivalent locking elements.

In the embodiment of the knife assembly shown in FIGS. 3C and 4G-H, knife pusher 94 is constructed of a stiff material, e.g., stainless steel, which is capable of withstanding the mechanical stress of the driving force directed against the knife assembly during actuation of the fastener applicator and encloses the upper section of knife holder 92. Other configurations of the knife pusher can also be used; thus e.g., this component can be provided as a strip of stress-resistant metal, e.g., stainless steel, covering only the top edge of the knife holder.

As shown in FIGS. 1A, 1B and 4, when actuator 70 is fully pivoted clockwise, driver 76, which carried by actuator 70, also is substantially parallel to the longitudinal axis of connecting structure 30. The distal end of driver 76 then extends into the proximal side of fastener holder 52 and is adjacent the proximal surface of knife pusher member 94 (FIG. 2) in the fastener holder. Safety latch 100 (FIG. 1A), which normally keeps actuator lever 110 pivoted clockwise away from handle 20, is now released by pivoting it counterclockwise. Lever 110 can now be pivoted counterclockwise about pivotal axis 112 toward handle 20, i.e., by squeezing it toward the handle with the fingers of the hand gripping the handle, to actuate the fastener driving mechanism.

When lever 110 is pivoted counterclockwise as just described, the end of lever 110 inside the proximal end of connecting structure 30 contacts the proximal end 78 of driver 76 and moves driver 76 in the distal direction. The distal end of driver 76 contacts the proximal surface of knife-fastener pusher member 93 (FIG. 2), thereby driving member 93 in the distal direction and causing it to drive fasteners 120 out of fastener holder 52 through tissue 12 and into retainers 130 held in anvil 54. Located slightly proximally of the distal end of fasteners 120 is knife element 91 of knife assembly 90 (see FIGS. 2, 3A-C and 4A-H). After fasteners 120 have begun to pierce tissue 12, knife 91 begins to cut the tissue and to assure a complete cut, is caused to superficially penetrate a cutting block (not shown) associated with anvil 54. As lever 110 is squeezed fully in the counterclockwise direction, fasteners 120 lock into retainers 130 and knife surface 61 completely severs tissue 12.

The joining of the tissue is now complete and all that remains to be done is to remove the fastened tissue from the instrument. This is accomplished by releasing lever 110 which, because leaf springs 69 biases knife-fastener pusher member 93 in the proximal direction, causes knife-fastener pusher member 93 to retract into fastener holder 52. Actuator 70 is rotated in the counterclockwise direction and fastener holder 52 pivots clockwise away from anvil 54 in response to the pressure of leaf spring 51. In addition, spring 81 biases alignment pin 80 away from anvil 54 and thus retracts pin 80 into fastener holder 52. Tissue 12 can now be readily withdrawn from the instrument. Cartridge 50 is now removed from the instrument by pulling anvil 54 out of distal leg 44. The expended cartridge can be discarded and another cartridge is loaded in the instrument if additional tissue fastening is required during the surgical procedure. When the surgical procedure is completed, instrument 10, if of the disposable type, is safely discarded or, if of the reusable type, is cleaned and sterilized to prepare it for use in another surgical procedure.

It will be understood that the embodiment shown and described herein is only illustrative of the principles of the invention, and that various modifications can be made by those skilled in the art without departing from the scope and spirit of the invention. In particular, the invention has been described in conjunction with a fastener cartridge featuring an improved tissue cutting knife assembly and a permanent, reusable actuator device. The invention could also have been described in conjunction with a fully disposable instrument. When the entire instrument is disposable, as much of the instrument as possible can be constructed from relatively inexpensive materials such as plastic, or the like and only those parts of the instrument which are subjected to relatively high mechanical stress need be made of metal.

What is claimed is:

1. In a surgical fastener cartridge which is adapted for use with an actuator apparatus having a rigid frame and a generally U-shaped protion for receiving the fastener cartridge, the actuator apparatus actuating the fastener cartridge to apply substantially parallel rows of fasteners to the tissue on both sides of a line of incision formed by a body tissue cutting knife assembly included within the fastener cartridge, said fastener cartridge possessing:
    (a) a fastener holder containing a quantity of fasteners, the fasteners being driven, upon actuation of the fastener cartridge, through substantially parallel rows of apertures defined upon a fastener ejecting surface of the fastener holder;
    (b) an anvil having a surface opposed to the fastener ejecting surface of the fastener holder and, upon actuation of the fastener cartridge, cooperating therewith to apply substantially parallel rows of fasteners to body tissue positioned between thef astener holder and anvil;
    (c) means for driving the fasteners through the apertures upon actuation of the fastener cartridge;
    (d) a tissue cutting knife assembly including (i) a knife element having an upper non-cutting edge and a lower cutting edge, (ii) a knife holder engaging the upper edge of the knife element and (iii) a knife pusher enclosing the knife holder, the cutting edge of the knife element being recessed within the fastener holder in the non-actuated condition of the fastener cartridge and, upon actuation of the fastener cartridge, extending beyond a slot formed between the rows of apertures; and,
    (e) means for driving the cutting edge of the knife assembly through the slot upon actuation of the fastener cartridge,
    the improvement which comprises a knife holder having two opposed sides defining at their lower sections a groove therebetween, the knife element being received into, and held in permanent and irreversible locking engagement with, the groove.

2. The surgical fastener cartridge of claim 1 wherein the groove of the knife holder possesses one or more locking elements which provide locking engagement with the upper edge of the knife element.

3. The surgical fastener cartridge of claim 2 wherein the groove of the knife holder possess one or more locking elements which cooperate with corresponding key elements formed upon the upper edge of the knife element to provide permanent and irreversible locking engagement therewith.

4. The surgical fastener cartridge of claim 3 wherein the knife holder is fabricated from a single piece of thermoplastic having two opposed sides joined through one or more hinge elements capable of at least one full flexure.

5. The surgical fastener cartridge of claim 4 wherein the thermoplastic is a polycarbonate.

6. The surgical fastener cartridge of claim 2 wherein the knife holder is fabricated from a single piece of thermoplastic having two opposed sides joined through one or more hinge elements capable of at least one full flexure.

7. The surgical fastener cartridge of claim 6 wherein the thermoplastic is a polycarbonate.

8. The surgical fastener cartridge of claim 1 wherein the knife holder is fabricated from a thermoplastic.

9. The surgical fastener cartridge of claim 1 wherein the knife holder is fabricated from a single piece of thermoplastic having two opposed sides joined through one or more hinge elements capable of at least one full flexure.

10. The surgical fastener cartridge of claim 9 wherein the thermoplastic is a polycarbonate.

* * * * *